(12) United States Patent
Sliski et al.

(10) Patent No.: US 7,208,748 B2
(45) Date of Patent: Apr. 24, 2007

(54) PROGRAMMABLE PARTICLE SCATTERER FOR RADIATION THERAPY BEAM FORMATION

(75) Inventors: Alan Sliski, Lincoln, MA (US); Kenneth Gall, Harvard, MA (US)

(73) Assignee: Still River Systems, Inc., Littleton, MA (US)

( * ) Notice: Subject to any disclaimer, the term of this patent is extended or adjusted under 35 U.S.C. 154(b) by 111 days.

(21) Appl. No.: 10/949,734

(22) Filed: Sep. 24, 2004

(65) Prior Publication Data

US 2006/0017015 A1 Jan. 26, 2006

Related U.S. Application Data

(60) Provisional application No. 60/590,088, filed on Jul. 21, 2004.

(51) Int. Cl.
*A61N 5/10* (2006.01)

(52) U.S. Cl. .............. 250/492.3; 250/519.1; 250/43.5 R; 250/517.1; 600/407

(58) Field of Classification Search .............. 250/492.3
See application file for complete search history.

(56) References Cited

U.S. PATENT DOCUMENTS

| | | | | |
|---|---|---|---|---|
| 3,679,899 A | * | 7/1972 | Dimeff | 250/343 |
| 5,440,133 A | * | 8/1995 | Moyers et al. | 250/492.3 |
| 5,818,058 A | * | 10/1998 | Nakanishi et al. | 250/492.3 |
| 5,851,182 A | * | 12/1998 | Sahadevan | 600/407 |
| 5,929,458 A | * | 7/1999 | Nemezawa et al. | 250/519.1 |
| 6,061,426 A | * | 5/2000 | Linders et al. | 378/149 |
| 6,777,700 B2 | | 8/2004 | Yanagisawa et al. | |
| 6,891,177 B1 | * | 5/2005 | Kraft et al. | 250/505.1 |

OTHER PUBLICATIONS

Coutrakon, G. et al., "A prototype beam delivery system for the proton medical accelerator at Loma Linda," *Med. Phys.* 18(6):1093-1099 (Nov./Dec. 1991).

Koehler, A.M. et al., "Range Modulators for Protons and Heavy Ions," *Nuclear Instruments and Methods* 131:437-440 (1975).

* cited by examiner

*Primary Examiner*—David Vanore
*Assistant Examiner*—Phillip A. Johnston
(74) *Attorney, Agent, or Firm*—Hamilton, Brook, Smith & Reynolds, P.C.

(57) ABSTRACT

Interposing a programmable path length of one or more materials into a particle beam modulates scattering angle and beam range in a predetermined manner to create a predetermined spread out Bragg peak at a predetermined range. Materials can be "low Z" and "high Z" materials that include fluids. A charged particle beam scatterer/range modulator can comprise a fluid reservoir having opposing walls in a particle beam path and a drive to adjust the distance between the walls of the fluid reservoir under control by a programmable controller. A "high Z" and, independently, a "low Z" reservoir, arranged in series, can be used. When used for radiation treatment, the beam can be monitored by measuring beam intensity, and the programmable controller can adjust the distance between the opposing walls of the "high Z" reservoir and, independently, the distance between the opposing walls of the "low Z" reservoir according to a predetermined relationship to integral beam intensity. Beam scattering and modulation can be done continuously and dynamically during a treatment in order to deposit dose in a target volume in a predetermined three dimensional distribution.

31 Claims, 7 Drawing Sheets

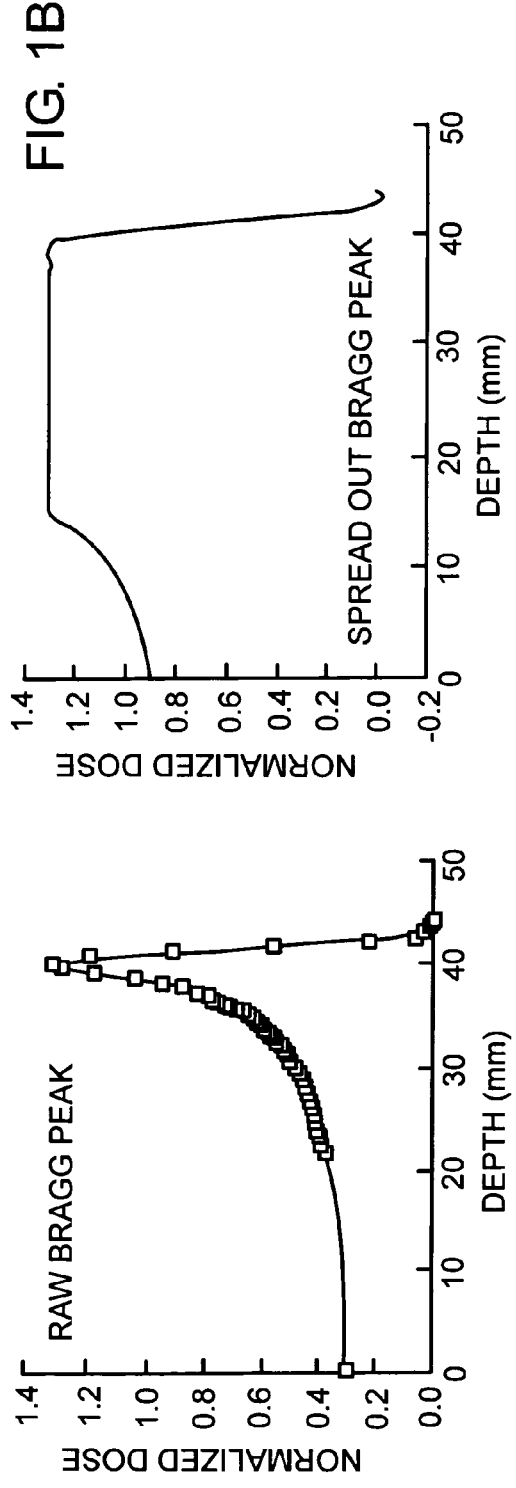
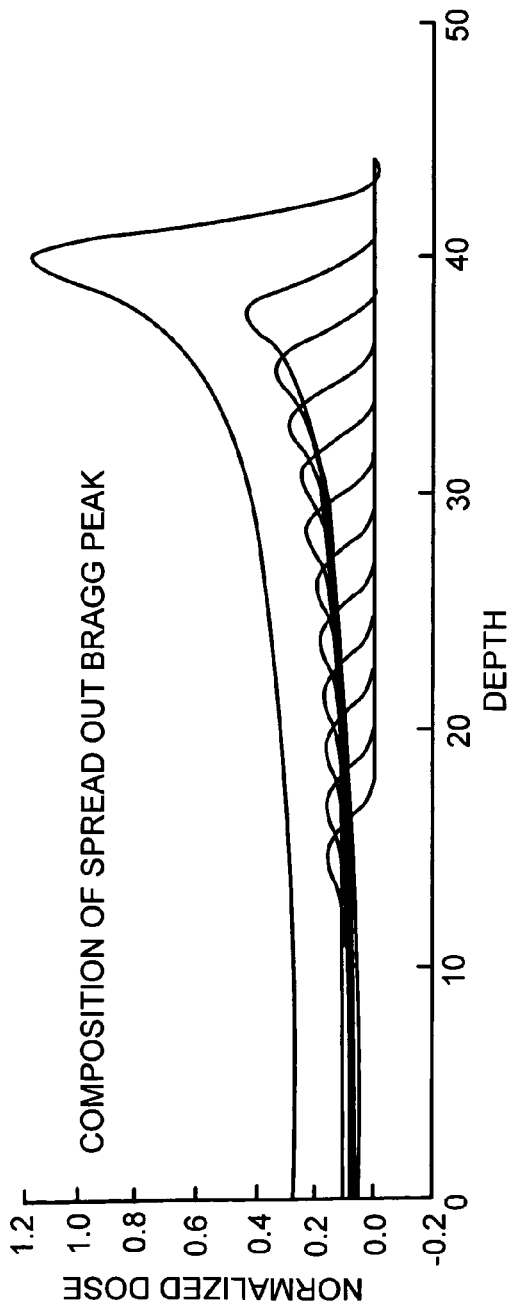
FIG. 1A
FIG. 1B
FIG. 1C

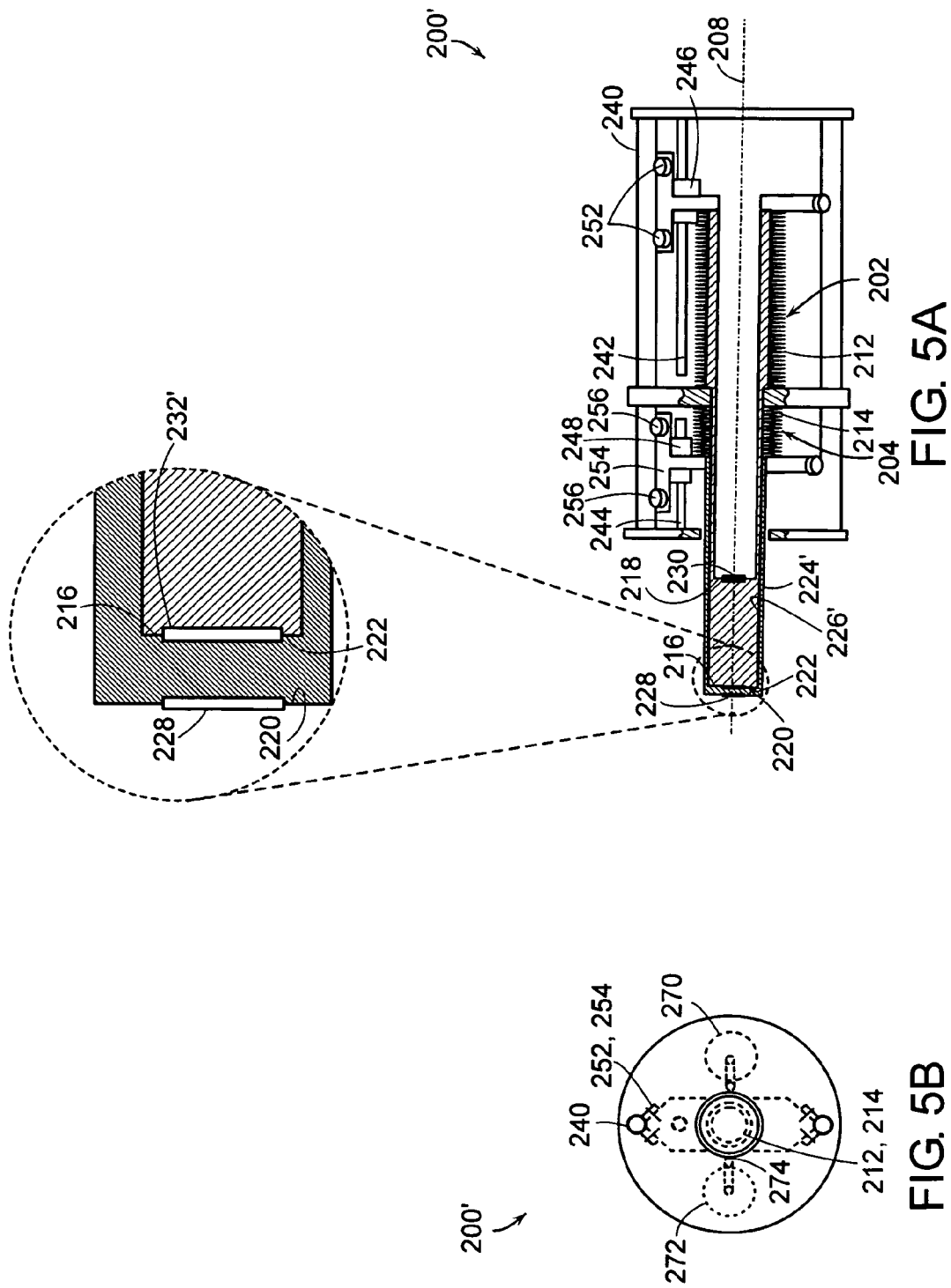

PROGRAMMABLE PARTICLE SCATTERER FOR RADIATION THERAPY BEAM FORMATION

RELATED APPLICATIONS

This application claims the benefit of U.S. Provisional Application No. 60/590,088, filed on Jul. 21, 2004. The entire teachings of the above application are incorporated herein by reference.

BACKGROUND OF THE INVENTION

Charged particles have been used in the field of radiation therapy for cancer for more than 50 years. In order to create a clinically useful dose distribution that conforms to the shape of the target volume within the patient, a number of beam shaping and modulating materials are interposed between the particle accelerator and the patient. A proton beam has a significant clinical advantage over conventional high energy x-ray beams which attenuate exponentially in tissue. The physics of the energy deposition is advantageous and different for protons compared to high energy x-rays (photons).

A proton beam delivers a small entrance dose, then delivers a large dose as the protons stop in the tissue. This large deposition of dose at the end of the tissue penetration range of the protons is called a Bragg peak, after the physicist who discovered the effect. FIG. 1 shows the Bragg peak from an unmodulated beam, as well as a spread out Bragg peak and the series of individual Bragg peaks that add together to make the spread out Bragg peak.

The beam, emerging from the particle accelerator, is shaped by inserting devices and materials into the beam. One objective of shaping the beam is to deliver a uniform dose of radiation throughout the volume of a target, such as a tumor in a patient's body. The range (i.e. the depth of beam penetration into the tissue) needs to be modulated to ensure that a uniform or other predetermined dose of radiation is delivered between the proximal and the distal surfaces of the target. (As used herein, the terms "proximal" and "distal" are used with respect to the beam path. The term "proximal" specifically refers to the area of entry of a beam into a target.) Furthermore, the beam needs to be spread out laterally in order to treat large tumors. (As used herein, the terms "lateral" refers to any direction substantially perpendicular to the beam path.) The beam is manipulated and shaped by a series of scatterers and apertures.

In a beam shaping system, the beam is first directed at a first scatterer/range modulator, which scatters the proton beam through an angle wide enough to treat a therapy field of about 20–30 cm. Following scattering and range modulation by the first scatterer, the beam is directed to a compensated second scatterer. The purpose of this element is to flatten the cross section of the beam emerging from the first scatterer. This allows the Bragg peak to be planar and uniform in intensity at the isocenter distance. FIG. 2 shows a compensated second scatterer that is comprised of high Z and low Z materials with shapes that match the scattering property of the high Z material with the absorption properties of the low Z material in order to provide a flat, uniform broad beam.

The third element of the beam shaping system is a range matching bolus. This is typically a thick cylinder of acrylic plastic into which the inverse of the 3-dimensional shape of the distal surface of the target volume has been machined. This element also includes a correction for the profile of the external surface of the patient from the beam direction and a correction for the inhomogenieties such as bone or air in the path. Most tissue is substantially equivalent to water, but corrections for these different materials can be calculated from the CT image data set. The resulting three dimensional structure is placed in the beam path to ensure that the Bragg peak conforms to the distal surface of the target, resulting in minimum dose to critical structures located beyond the target volume.

The fourth element of the beam shaping system shapes the beam laterally to match the shape of the target volume as seen from the direction of the beam's origin by using apertures made specifically for that treatment. This is usually accomplished by machining a profiled aperture into a thick piece of brass or other high Z material and placing it in close proximity to the patient. The beam is limited in lateral extent by this element and therefore conforms to the shape of the target volume.

SUMMARY OF THE INVENTION

Interposing a programmable path length of one or more scattering and/or absorbing materials into a particle beam may be used to modulate scattering angle and beam range in a predetermined manner. A charged particle beam scatterer/range modulator can comprise high Z material, having an adjustable path length in a particle beam path, low Z material having an adjustable path length in the particle beam path, and a programmable controller that independently adjusts the high Z and low Z path lengths during exposure of a target to the beam. The high Z and the low Z materials can be liquid. The path length of the low Z material and, independently, the path length of the high Z material can be continuously adjustable.

The charged particle beam scatterer/range modulator can comprise a fluid reservoir having opposing walls in a particle beam path, a drive to adjust the distance between the walls of the fluid reservoir, and a programmable controller for the drive to adjust the distance between the walls of the reservoir during exposure of a target to the beam. The distance between the opposing walls of the reservoir can be continuously adjustable. A first and second fluid reservoir can be arranged in series in the particle beam path. The first and the second reservoirs can independently contain high Z and low Z materials. The distance between the opposing walls of the first reservoir and, independently, the distance between the opposing walls of the second reservoir can be continuously adjustable.

A source of charged particles that provides a charged particle beam and a charged particle beam scatterer/range modulator can be employed in a radiation treatment apparatus. A beam monitor can be used to measure beam intensity and communicate beam intensity to the programmable controller. The programmable controller can adjust the low Z and, independently, the high Z path lengths according to a predetermined relationship between the time integral of the beam intensity and the desired path lengths of the low Z and high Z materials. The programmable controller can adjust the low Z and, independently, the high Z path lengths continuously and dynamically.

The source of charged particles can be a cyclotron. The cyclotron can be a synchrocyclotron. Any charged particles may be used, for example, the charged particles can be protons.

The high Z material and the low Z material of a charged particle beam scatterer/range modulator can be disposed in an extraction channel of the synchrocyclotron. Where the charged particle beam scatterer/range modulator comprises a fluid reservoir, having opposing walls in a particle beam path, such fluid reservoir can similarly be disposed in an extraction channel of the synchrocyclotron.

Embodiments of the present invention have a number of advantages. By independently and continuously changing thicknesses of high Z and low Z material, the path of the particle can be varied continuously over the course of a treatment. This can effectively produce uniquely variable, substantially arbitrary profiles of spread out Bragg peaks, thus delivering both a conformal and a non-uniform dose of radiation to the target. The first scatterer/range modulator of the present invention matches the dose deposition by the beam to the treatment volume in three dimensions, resulting in a highly conforming dose distribution. This leads to the best clinical outcome for the patient. The local control rate of the cancer treatment increases with increasing dose to the tumor, while the complication rate (due to unnecessary dose to critical structures) increases with the dose given to the surrounding normal tissue. By using a precisely shaped proton beam, the ratio of treatment volume dose to the dose given to surrounding tissue is increased markedly over treatments given with photon (x-ray) beams.

The use, in some embodiments, of synchrocyclotron as a source of charged particles allows the present invention to avoid relying on a variable energy beam. Furthermore, the operation of the device of the present invention can be controlled by a programmable processor in a continuously variable manner by adjusting the timing of the motion of the high Z and low Z materials to generate a predetermined, non-uniform spread out Bragg peak.

In addition to the regular clinical scenarios, there is at least one special case of scattering and range modulation where a higher intensity, small beam is required, such as in the case of treating eye tumors or macular degeneration. These special cases have a shallow depth of penetration, a very small field size and the treatment time is to be minimized. In this case, the second compensated scatterer is not employed, as the field size is very small. The first scatterer/range modulator of the instant invention is particularly advantageous for this special case application.

This invention uses the underlying physical principles employed in the past and combines them with modern control system technology and a novel geometry to create a novel beam scattering and range modulation apparatus that can programmatically deliver not only the same performance as fixed scatterer/modulator components, but also uniquely variable profiles modulated in time to generate dose distributions that can be more highly conformal to the target volume. The ability to continuously and independently vary the beam path lengths through the "high Z" and "low Z" materials avoids the problem of having to plan and deliver a treatment does of radiation in a finite number of fixed spread out Bragg peaks.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1A is a representative plot showing the deposited dose of radiation delivered by a proton beam as a function of depth of penetration. The peak at the distal portion of the range of penetration is the Bragg peak.

FIG. 1B is a plot that shows a "spread out" Bragg peak that is desired for delivery of a conformal dose of radiation.

FIG. 1C is a plot that shows the result of superposition of several Bragg peaks produced by proton beams with modulated range of penetration.

FIG. 5A is a is a side view (partially cut away) of a variation in the preferred embodiment of a charged particle scatterer/range modulator of the present invention.

FIG. 5B is an end view of the device of FIG. 6A.

DETAILED DESCRIPTION OF THE INVENTION

Although this invention is applicable to all charged particle beams, this discussion will focus on proton beams for radiation therapy as an illustrative and advantageous example.

As discussed above, the proton beam emerging from a particle accelerator is shaped and modulated by a number of devices and material interposed in the beam path.

Figure 3:
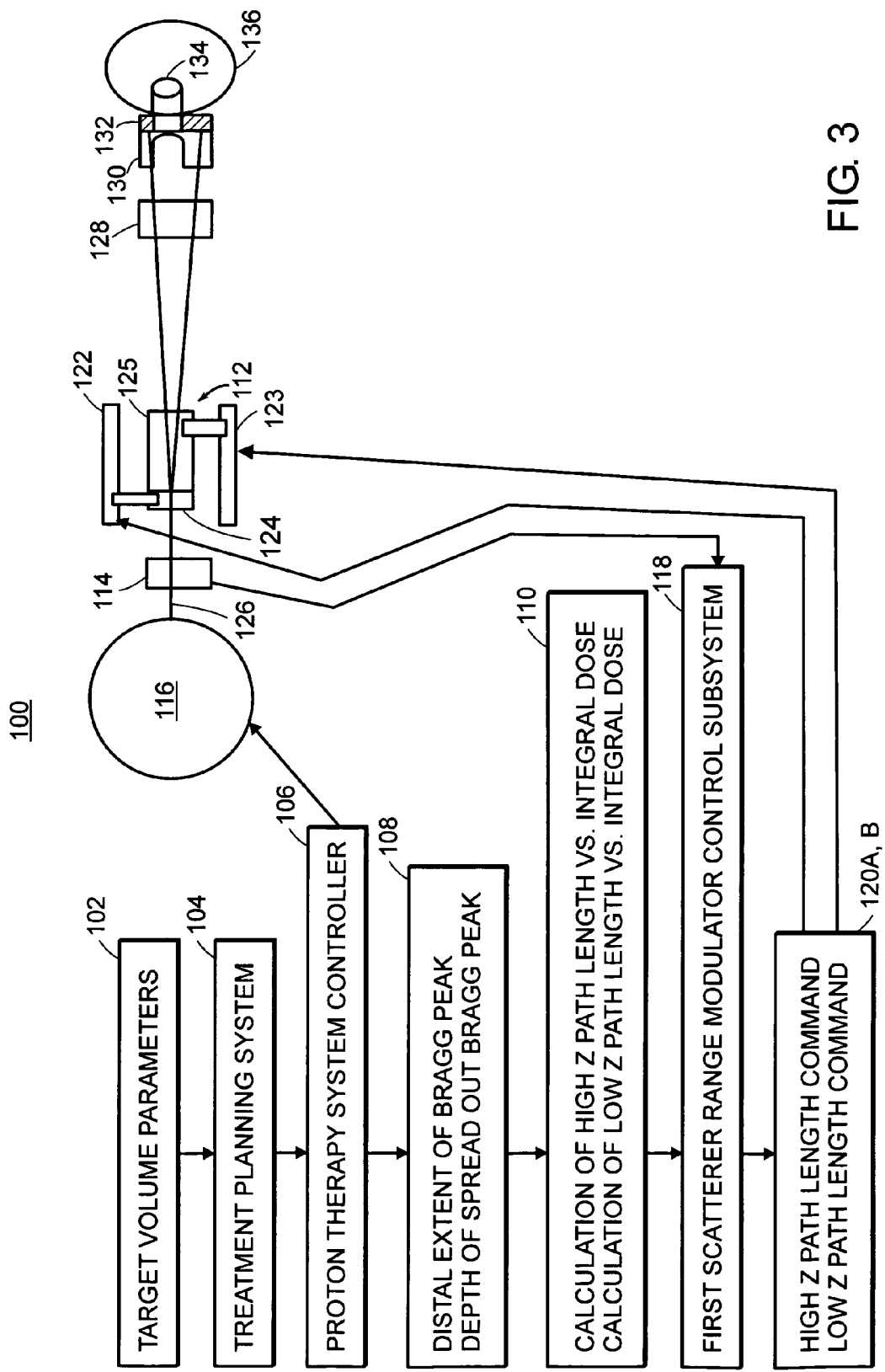
FIG. 3 is a block-diagram of a radiation treatment system that employs devices and methods of the present invention.

An embodiment of the present invention is a charged particle scatterer/range modulator, that, in some embodiments, can be used in common implementations of proton beam radiation therapy systems as a first scatterer. FIG. 3 is a block diagram of proton therapy system 100 incorporating embodiments of the present invention. It is simplified to illustrate the elements of the system that pertain to this invention. Other subsystems such as RF control system of the particle accelerator, vacuum, power supplies, etc. have been omitted for clarity.

The input 102 into the system 100 is, typically, the size and location of the target volume to be treated and the external contour of the patient. Target volume parameters 102 are used by the treatment planning system 104 to prescribe a three dimensional dose distribution to conformally deliver the dose to the target volume. The output of treatment planning system 104 is communicated to the proton therapy system controller 106, that generates a series of parameters used by different subsystems to implement the treatment. These parameters include distal extent of Bragg peak and depth of spread out Bragg peak 108 and calculations 110 of high and low Z path lengths as a function of integral dose, which are based on parameters 108. The parameters important to the subsystem comprising the programmable first scatterer/range modulator 112 are the path length of high and low Z material to be interposed into the proton beam as a function of integral dose as measured by the beam monitor 114. If the output of the accelerator 116 was known to be constant over time, the path length could be programmed with respect to time. In this embodiment, use of the information directly from the beam monitor 114 removes the constraint that the output of the accelerator be constant with time.

The calculated path lengths with corrections for the measured integral dose, are converted by first scatterer/range modulator control system 118 into high Z and low Z position commands 120 for linear actuators 122 and 123 that vary the path lengths 124 and 125 of the high Z and low Z materials, respectively. The high Z and low Z materials can be solid, liquid or gaseous. Liquid materials are preferred. In a preferred embodiment, linear actuators 122 and 123 are linear motors/encoders. The encoders measure the actual position and servo loops within the system (shown in greater detail with reference to FIG. 7) ensure tight control and error condition sensing to ensure safety and prevent errors in treatment by exercising tight control of low Z and high Z path lengths.

Figure 2:
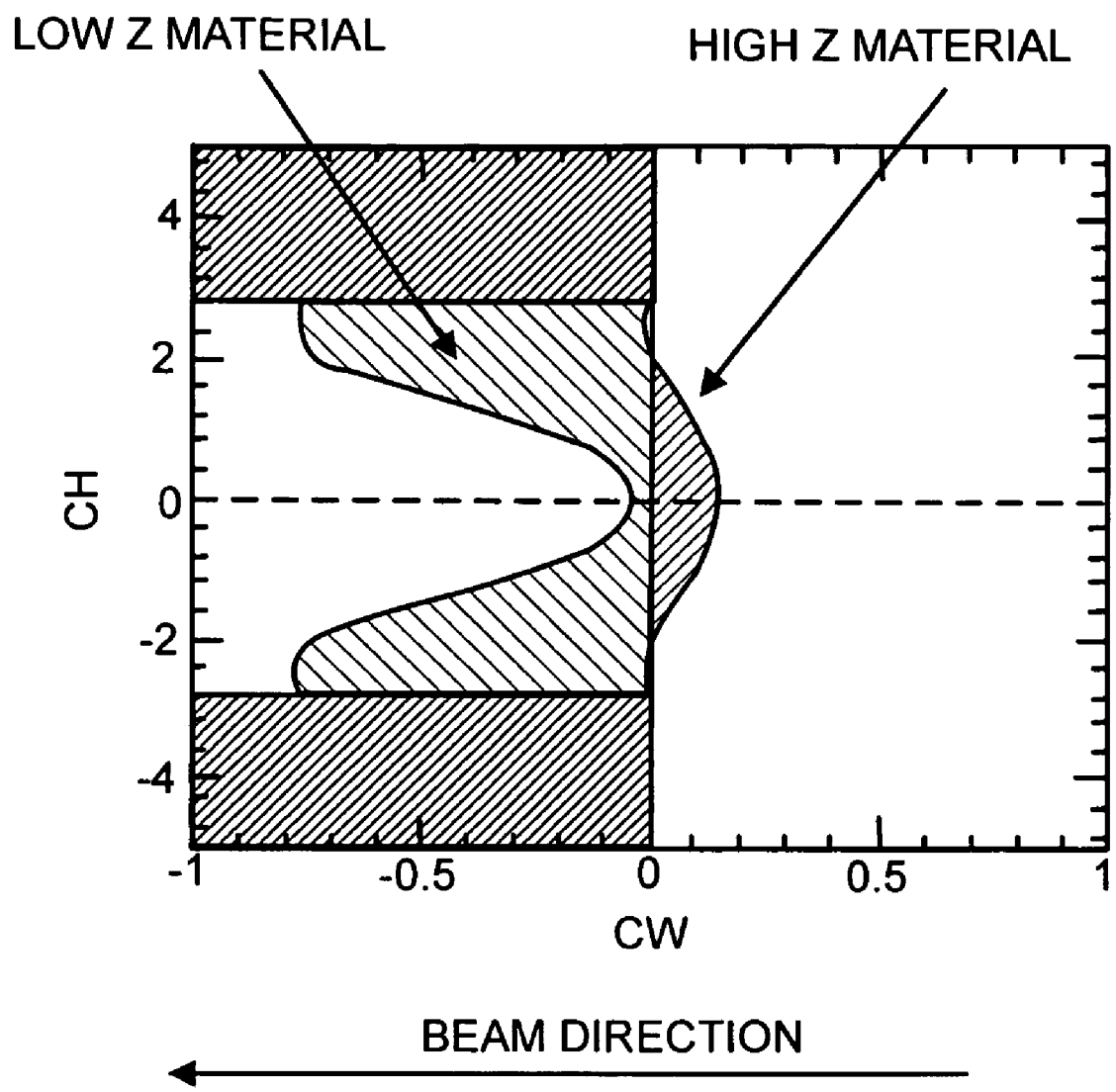
FIG. 2 shows the cross-section of a compensated second scatterer that is comprised of high Z and low Z materials with shapes that match the scattering and absorption properties of the materials.

Beam 126, produced by particle accelerator 116, which, in one embodiment, is a cyclotron, is monitored by beam monitor 114 and modulated by the first scatterer/range modulator of the present invention 112. After passing through the first scatterer 112, beam 126 passes through the second compensated scatterer 128, such as the one shown in FIG. 2.

Following continuing lateral expansion and beam conditioning at the second scatterer 128, beam 126 is further shaped by range compensating bolus 130 and, laterally, by final conformal aperture 132 before entering target volume 134 within patient 136.

Two alternative embodiments of first scatterer/range modulator 112 of FIG. 3 are devices 200 and 200', shown in FIGS. 4A and 4B and FIGS. 5A and 5B.

Figure 4A:
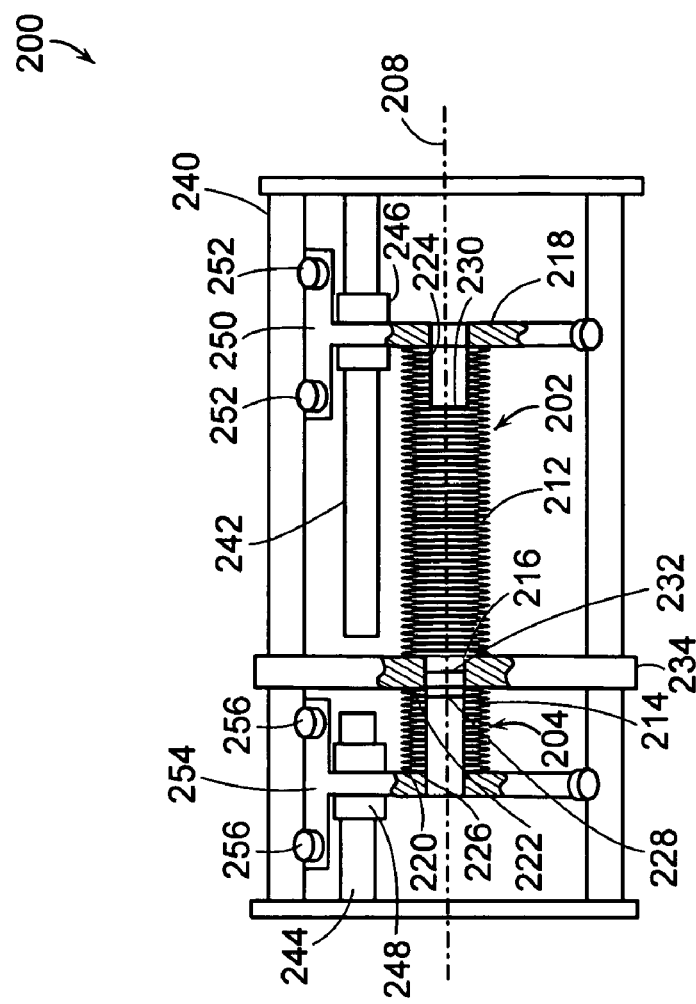
FIG. 4A is a side view (partially cut away) of the preferred embodiment of a charged particle scatterer/range modulator of the present invention.

Referring to FIGS. 4A and 5A, devices 200 and 200' comprise two sealed systems: system 202, filled with a low Z fluid, such as water, and system 204 filled with a high Z fluid, such as mercury in liquid state. The fluids cam also incorporate other elements in solution such as boron in the low Z fluid that may act as shielding for neutrons produced in the high Z section. The proton beam (not shown) travels along axis 208 from left to right. The two systems 202 and 204 are arranged in series. Either the high Z system 204 or the low Z system 202 can be located nearest to the source of the proton beam. The embodiments shown here have the high Z system 204 located nearest the output of the accelerator 116 (see FIG. 3 or FIG. 6).

To provide reliable fluid sealing over a long life, the systems 202 and 204 include welded metal bellows 212 and 214, respectively. Bellows 212 and 214 function as expandable side walls that, together with the opposing walls 216, 218 (system 202) and 220, 222 (system 204), form fluid reservoirs of adjustable volume disposed in a particle beam path. Referring to device 200 as shown in FIG. 4A, within each reservoir, there are re-entrant tubular extensions 224 and 226. Referring to device 200' as shown in FIG. 5A, the tubular extensions 224' and 226' are coaxial, with tubular extension 226' disposed within tubular extension 224'. Referring to device 200' as shown in FIG. 5A, opposing walls 216 and 222 are different surfaces of the same portion of tubular extension 226'. Side wall 220 holds entrance window 228. Side wall 218 holds exit window 230. The entrance and exit windows 228 and 230 are made of thin radiation-resistant foil made of, for example, stainless steel or titanium. The foil is thin enough to not substantially affect the beam.

Referring to device 200 as shown in FIG. 4A, a thin, radiation resistant septum 232, made from material similar to those of windows 228 and 230, is disposed across an aperture within central plate 234. Referring to device 200', as shown in FIG. 5A, septum 232' is disposed across an aperture in the portion of tubular extension 226' that defines walls 216 and 222. Septum 232 separates the two fluids in systems 202 and 204. A small correction for the thickness of septum 232 and windows 228, 230 would be accounted for in the modeling of the system.

Referring to device 200 as shown in FIG. 4A, during the operation of the bellows 212 and 214, entrance and exit windows 228 and 230 can touch the dividing septum 232. Likewise, referring to device 200' as shown in FIG. 5A, entrance and exit windows 228 and 230 can touch the dividing septum 232'. This allows either the high Z path length or, independently, the low Z path length to be chosen as substantially zero. An allowance for further compression of the bellows 212 and 214 is made to allow the entrance and exit windows 228 and 230 to touch the dividing septum 232 or 232' before the bellows 212 and 214 are fully compressed.

Linear bearings rail 240 constrains the motion of the bellows 212 and 214 and extensions 226, 226' and 224, 224' to be substantially co-linear with the particle beam axis 208.

A pair of linear motors/encoder, such as actuators 122 and 124 shown in FIG. 3, are used to change low Z and high Z path lengths. Referring to FIGS. 4A and 5A, the linear motors/encoders include stators 242 and 244, substantially parallel to beam axis 208, and motor/encoders carriages 246 and 248 that move along stators 242, 244. Attached to motor/encoder carriage 246 and to low Z bellows 212 is ball bearing carriage 250 that moves along linear rail 240 using ball bearings 252. Similarly, ball bearing carriage 254 is attached to motor/encoder carriage 248 and to high Z bellows 214. Ball bearing carriage 254 moves along linear rail 240 using ball bearings 256. Movement of motor/encoder carriages 246 and 248 expands or contracts bellows 212 and 214, changing the amounts of high Z and low Z fluids filling the respective bellows and thus changing the high Z and low Z path lengths.

Figure 4B:
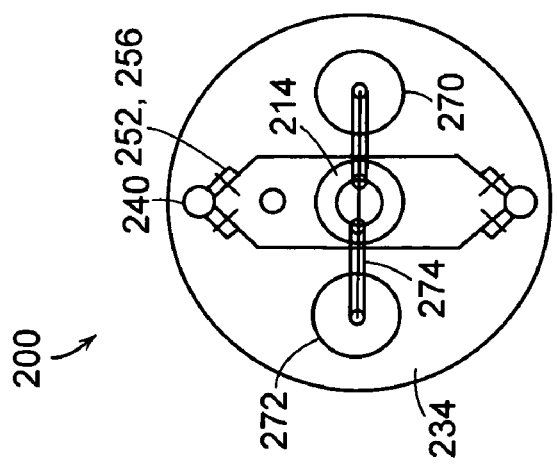
FIG. 4B is an end view of the device of FIG. 4A.

The fluids in the bellows are substantially incompressible. Therefore, provision is made for a set of expansion reservoirs, also constructed of welded metal bellows in this embodiment. Referring to FIGS. 4B and 5B, expansion reservoirs 270 and 272 are adjacent to bellows 212 and 214. Expansion reservoirs 270 and 272 are connected by way of internal passages 274 in the central plate 234. As the path length of either fluid is varied by means of the control system 118, the displaced fluid is accommodated in the corresponding expansion reservoir. The driven bellows 212 and 214 and the expansion reservoirs 270 and 272 comprise a sealed system with no sliding or wearing seals that tend to deteriorate and leak over time and in proximity to scattered radiation. The reliability of the sealed systems can be predicted from the fatigue properties of the materials chosen for the bellows and can be made effectively infinite if the design stress does not exceed the endurance limit of the material. This is important when using a material such as mercury in a hospital environment.

Figure 6:
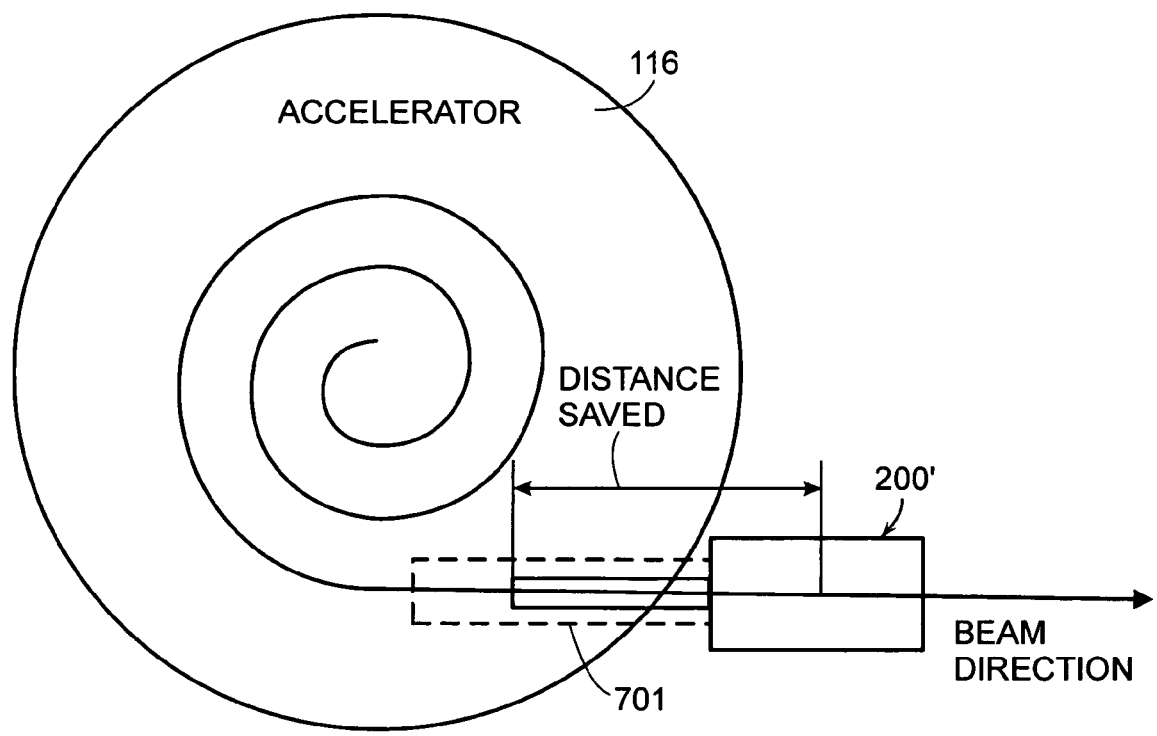
FIG. 6 is a plan view showing the advantageous positioning of the embodiment shown in FIG. 5A when combined with a particle accelerator.

Referring to FIG. 6, by nesting tubular extensions 224' and 226' of device 200' as shown in FIG. 5A, the scattering fluids can be placed closer to a particle beam source, such as accelerator 116, than otherwise would be possible for device 200. As shown in FIG. 6, tubular extensions 224' and 226' can be inserted into extraction channel 701, allowing a more compact overall system. It is noted that tubular extensions 224' and 226' are preferably magnetically shielded. The principles of operation and the function of individual elements of the unit are identical to the embodiment shown in FIGS. 4A and 4B.

Referring again to FIG. 3, control system 118 drives the motors 122 and 123 and receives signals from the motor/encoder carriages (246 and 248 on FIGS. 4A and 5A) to precisely control the position and velocity of the entrance and exit windows 228, 230 with respect to septum 232 (see FIGS. 4A and 5A). This translates into controlling the amount of high Z and low Z material in the path of the particle beam, thus controlling the scattering angle and range of the particle beam in a pre-determined manner. The path lengths of high Z and low Z material 124 and 125, and therefore the positions of the motor/encoder carriages (246 and 248 in FIGS. 4A and 5A) are also a function of integral dose or radiation, measured by the beam monitor 114. Accordingly, one embodiment, the present invention includes a feedback control loop 300, shown in FIG. 7.

Figure 7:
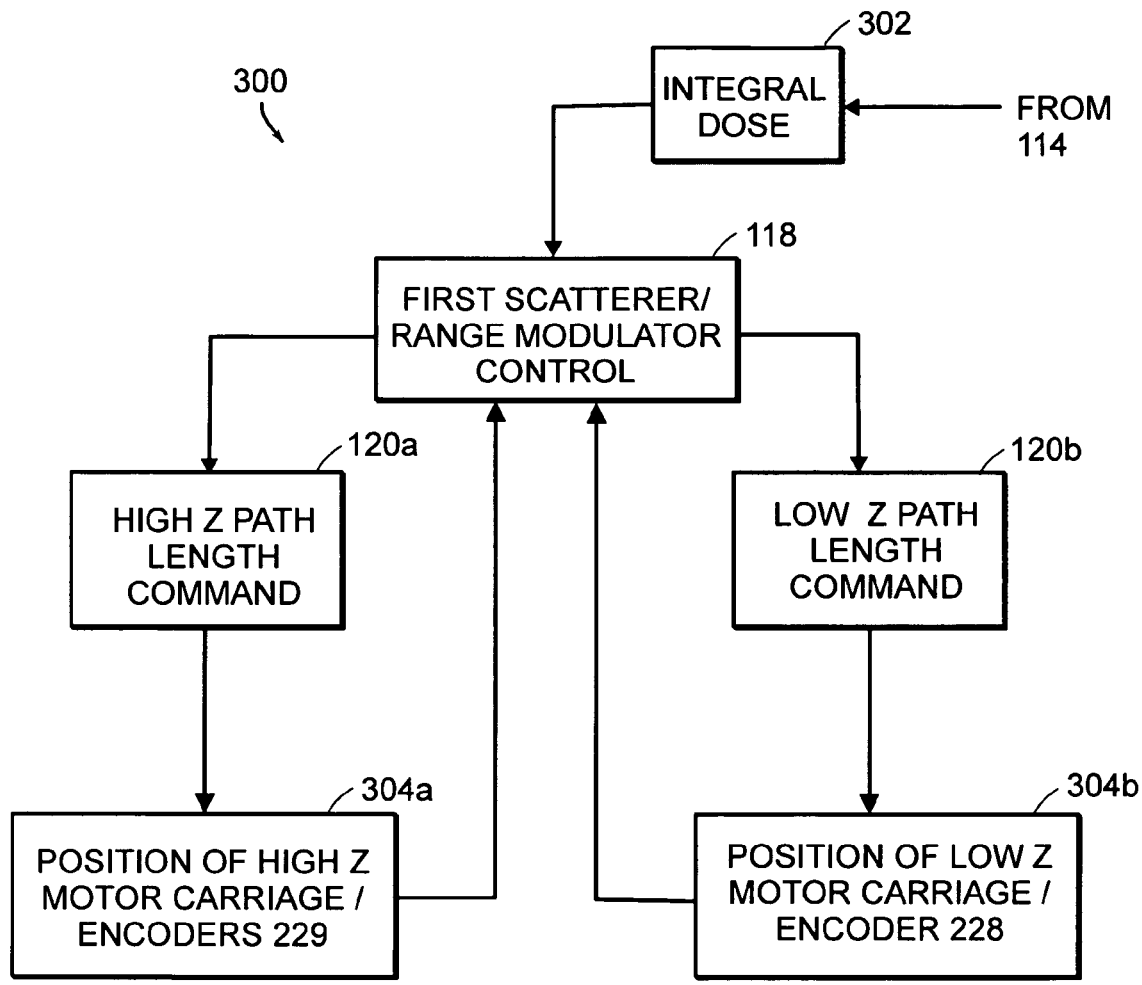
FIG. 7 is a block-diagram illustrating the feedback control loop employed by the preferred embodiment of a method of the present invention.

Referring to FIG. 7, the integral dose of delivered radiation is computed at step 302 based on measurements by beam monitor 114. Based on the integral dose, first scatterer/range modulator control system 118 produces high Z and low Z position commands at steps 120a and 120b, respectively. These commands are transmitted to linear actuators/motors (122 and 123 in FIG. 3), which change the positions of high Z and low Z motor carriages/encoders (246 and 248 in FIGS. 4A and 5A). At steps 304a and 304b, the encoders measure the actual position of the carriages and transmit this data to first scatterer/range modulator control 118. Thus, feedback control loop 300 is used, in response to beam intensity output, to continuously, dynamically (i.e. in real time) and independently adjust the distance between entrance window 228 and septum 232 within high Z system 204 and septum 232 and exit window 230 within low Z system 202 (see FIGS. 4A and 5A). Accordingly, the low Z and the high Z path lengths are continuously, dynamically and independently adjusted according to beam intensity.

While this invention has been particularly shown and described with references to preferred embodiments thereof, it will be understood by those skilled in the art that various changes in form and details may be made therein without departing from the scope of the invention encompassed by the appended claims.

What is claimed is:

1. A charged particle beam scatterer/range modulator comprising: a liquid high Z material having an adjustable path length in a particle beam path; in series with a low Z material having an adjustable path length in the particle beam path; and a programmable controller that independently adjusts the high Z and low Z path lengths during exposure of a target to the beam.

2. The scatterer/modulator of claim 1 wherein the path length of the low Z material and, independently, the path length of the high Z material are continuously adjustable.

3. The scatterer/modulator of claim 1 wherein the charged particles are protons.

4. A radiation treatment apparatus, comprising: a source of charged particles that provides a charged particle beam; and a charged particle beam scatterer/range modulator, that includes a liquid high Z material having an adjustable path length in a particle beam path; in series with a liquid low Z material having an adjustable path length in the particle beam path; and a programmable controller that independently adjusts the high Z and low Z path lengths during exposure of a target to the beam.

5. The apparatus of claim 4 wherein the path length of the low Z material and, independently, the path length of the high Z material are continuously adjustable.

6. The apparatus of claim 4 wherein the charged particles are protons.

7. The apparatus of claim 4 wherein the source is a cyclotron.

8. The apparatus of claim 7 wherein the cyclotron is a synchrocyclotron.

9. The apparatus of claim 4 further including
a beam monitor for measuring particle beam intensity, the beam monitor communicating beam intensity to the programmable controller, the programmable controller adjusting the low Z and, independently, the high Z path lengths according to integral beam intensity.

10. The apparatus of claim 9 wherein the programmable controller adjusts the low Z and, independently, the high Z path lengths continuously and dynamically.

11. A method of scattering and/or modulating a range of a charged particle beam, comprising: directing a charged particle beam through a liquid high Z material having an adjustable path length in a particle beam path; directing the charged particle beam through a liquid low Z material having an adjustable path length in the particle beam path; wherein the high Z and low Z materials are in series; and independently adjusting the high Z and low Z path lengths during exposure of a target to the beam under control by a programmable controller.

12. The method of claim 11 wherein the path length of the low Z material and, independently, the path length of the high Z material are continuously adjustable.

13. The apparatus of claim 11 wherein the charged particles are protons.

14. The method of claim 11 further including
measuring particle beam intensity; and
with the programmable controller adjusting the low Z and, independently, the high Z path lengths according to beam intensity.

15. The method of claim 14 wherein the programmable controller adjusts the low Z and, independently, the high Z path lengths continuously and dynamically.

16. A method of treating a patient by directing a charged particle beam at a target within said patient, comprising: producing a charged particle beam; directing the charged particle beam through a liquid high Z material having an adjustable path length in a particle beam path; directing the charged particle beam through a liquid low Z material having an adjustable path length in the particle beam path; wherein the high Z and low Z materials are in series; and independently adjusting the high Z and low Z path lengths during exposure of a target to the beam under control by a programmable controller.

17. The method of claim 16 wherein the path length of the low Z material and, independently, the path length of the high Z material are continuously adjustable.

18. The method of claim 16 wherein the charged particles are protons.

19. The method of claim 16 wherein the charged particle beam is produced by a cyclotron.

20. The method of claim 19 wherein the cyclotron is a synchrocyclotron.

21. The method of claim 16 further including
measuring beam intensity; and
with the programmable controller adjusting the low Z and, independently, the high Z path lengths according to beam intensity.

22. A radiation treatment apparatus, comprising: a synchrocyclotron that provides a charged particle beam; and a charged particle beam scatterer/range modulator, that includes liquid high Z material in an extraction channel of the synchrocyclotron having an adjustable path length in a particle beam path; in series with a liquid low Z material in an extraction channel of the synchrocyclotron having an adjustable path length in the particle beam path; and a programmable controller that independently adjusts the high Z and low Z path lengths during exposure of a target to the beam.

23. The apparatus of claim 22 wherein the path length of the low Z material and, independently, the path length of the high Z material are continuously adjustable.

24. The apparatus of claim 22 wherein the charged particles are protons.

25. The apparatus of claim 22 further including
a beam monitor for measuring particle beam intensity, the beam monitor communicating beam intensity to the programmable controller, the programmable controller adjusting the low Z and, independently, the high Z path lengths according to integral beam intensity.

26. The apparatus of claim 25 wherein the programmable controller adjusts the low Z and, independently, the high Z path lengths continuously and dynamically.

27. A radiation treatment apparatus, comprising: a synchrocyclotron that provides a charged particle beam; and a charged particle beam scatterer/range modulator, that includes high Z material in an extraction channel of the synchrocyclotron having an adjustable path length in a particle beam path; low Z material in an extraction channel of the synchrocyclotron having an adjustable path length in the particle beam path; wherein the high Z and low Z materials are in series; and a programmable controller that independently adjusts the high Z and low Z path lengths during exposure of a target to the beam.

28. The method of claim 27 wherein the path length of the low Z material and, independently, the path length of the high Z material are continuously adjustable.

29. The apparatus of claim 27 wherein the charged particles are protons.

30. The method of claim 27 further including
measuring particle beam intensity; and
with the programmable controller adjusting the low Z and, independently, the high Z path lengths according to beam intensity.

31. The method of claim 30 wherein the programmable controller adjusts the low Z and, independently, the high Z path lengths continuously and dynamically.

* * * * *

UNITED STATES PATENT AND TRADEMARK OFFICE
CERTIFICATE OF CORRECTION

PATENT NO. : 7,208,748 B2
APPLICATION NO. : 10/949734
DATED : April 24, 2007
INVENTOR(S) : Alan Sliski and Kenneth Gall It is certified that error appears in the above-identified patent and that said Letters Patent is hereby corrected as shown below:

Column 9 and 10

Lines 26-27 and 1-9, delete

"27. A radiation treatment apparatus, comprising: a synchrocyclotron that provides a charged particle beam; and a charged particle beam scatterer/range modulator, that includes high Z material in an extraction channel of the synchrocyclotron having an adjustable path length in a particle beam path; wherein the high Z and low Z materials are in series; and a programmable controller that independently adjusts the high Z and low Z path lengths during exposure of a target to the beam." and insert --27. A method of scattering and/or modulating a range of a changed particle beam, comprising:
  producing a particle beam in a synchrocyclotron;
  directing the charged particle beam through a liquid high Z material having an adjustable path length in a particle beam path and disposed in an extraction channel of the synchrocyclotron;
  directing the charged particle beam through a liquid low Z material, in series with the liquid high Z material, and having an adjustable path length in the particle beam path and disposed in the extraction channel of the synchrocyclotron; and
  independently adjusting the high Z and low Z path lengths during exposure of a target to the beam under control by a programmable controller.--

Signed and Sealed this

Eighteenth Day of December, 2007

JON W. DUDAS
*Director of the United States Patent and Trademark Office*

UNITED STATES PATENT AND TRADEMARK OFFICE
CERTIFICATE OF CORRECTION

PATENT NO. : 7,208,748 B2  
APPLICATION NO. : 10/949734  
DATED : April 24, 2007  
INVENTOR(S) : Alan Sliski and Kenneth Gall It is certified that error appears in the above-identified patent and that said Letters Patent is hereby corrected as shown below:

Column 10

Line 14, delete "apparatus," and insert --method--;

Signed and Sealed this

Third Day of June, 2008

JON W. DUDAS  
*Director of the United States Patent and Trademark Office*